United States Patent [19]

Mascarenhas

[11] Patent Number: 5,086,169

[45] Date of Patent: Feb. 4, 1992

[54] ISOLATED POLLEN-SPECIFIC PROMOTER OF CORN

[75] Inventor: Joseph P. Mascarenhas, Delmar, N.Y.

[73] Assignee: The Research Foundation of State University of New York, Albany, N.Y.

[21] Appl. No.: 429,822

[22] Filed: Oct. 31, 1989

Related U.S. Application Data

[63] Continuation-in-part of Ser. No. 341,151, Apr. 20, 1989, abandoned.

[51] Int. Cl.$^5$ .................... C12N 15/11; C12N 15/82
[52] U.S. Cl. .......................... 536/27; 935/6; 935/33; 935/35; 935/59; 435/172.3; 435/320.1
[58] Field of Search ............... 435/172.3, 320, 240.4, 435/91, 320.1; 536/27; 935/23, 33, 67, 6

[56] References Cited

U.S. PATENT DOCUMENTS 4,801,326 1/1989 Ackmann et al. .
4,803,165 2/1989 Appelbaum .

FOREIGN PATENT DOCUMENTS 0122791 4/1984 European Pat. Off. .
0126546 4/1984 European Pat. Off. .
0222526 5/1987 European Pat. Off. .
2187462 1/1987 United Kingdom .

OTHER PUBLICATIONS

Hess, (1971), Nafurwissenschaften, vol. 58 (7), p. 366 (Abstract relied on).
Vaeck et al. (1987), Anais da Sociedade. Entomologica de Brasil, vol. 16(2), pp. 427–435, Abstract relied on.
Lamppa, G. et al., Nature 316:750–752 (1985).
Rochester, D. E. et al., EMBO J. 5:451–458 (1986).
Nagy, F. et al., EMBO J. 5:1119–1124 (1986).
Guiltinan, M. J. et al., Mol. Gen. Genet. 207:328–334 (1987).
Koncz, C. et al., Proc. Nat'l. Acad. Sci. U.S.A. 84: 131–135 (1987).
Kuhlemeier, C. et al., Ann. Rev. Plant Physiol. 38:221–257 (1987).
Loesch-Fries, L. S. et al., EMBO J. 6:1845–1851 (1987).
Taylor, J. L. et al., Mol. Gen. Genet. 210:572–577 (1987).
Vaeck, M. et al., Nature 328:33–37 (1987).
Beachy, R. N. et al., in Current Communications in Molecular Biology, Genetic Improvements of Agriculturally Important Crops, R. T. Fraley, N. M. Frey and J. Schell, eds., Cold Spring Harbor Laboratory, pp. 47–53 (1988).
Marris, C. et al., Plant. Mol. Biol. 10: 359–366 (1988).
Knowlton, S. et al., in Current Communications in Molecular Biology, Genetic Improvements of Agriculturally Important Crops, R. T. Fraley, N. M. Frey and J. Schell, eds., Cold Spring Harbor Laboratory, pp. 55–60 (1988).
Leemans, J., in Current Communications in Molecular Biology, Genetic Improvements of Agriculturally Important Crops, R. T. Fraley, N. M. Frey and J. Schell, eds, Cold Spring Harbor Laboratory, pp. 77–81 (1988).

(List continued on next page.)

Primary Examiner—Elizabeth C. Weimar
Assistant Examiner—Gary Benzion
Attorney, Agent, or Firm—Heslin & Rothenberg

[57] ABSTRACT

The nucleotide sequence of the promoter region from pollen-specific genes of corn is disclosed. The sequence consists of at least 1315 base pairs upstream from a region of DNA which hybridizes to mRNA found only in pollen. In addition, a sequence of DNA containing over 500 base pairs downstream from the transcribed region has also been cloned and sequenced. The sequenced regions can be used to introduce into plants genes, the expression of which in pollen is desired. A suicide gene can be added to the 3' end of the promoter to induce abortion of pollen development and thereby product male sterile plants. Other genes coding for insect toxins or nutritional proteins can be expressed in pollen by use of the pollen-specific promoter.

1 Claim, 6 Drawing Sheets

PARTIAL RESTRICTION MAP OF GENOMIC CLONE Zmg 13 SHOWING CODING AND PROMOTER REGIONS, AND REPRESENTATIVE SUBCLONES (a, b, c, d)

A=ScaI; B=BamHI; C=ClaI; D=DraI; E=NaeI; H=HindIII; K=SacI; M=SmaI; P=PvuII; S=SalI; X=XhoI; ◄---► =EMBL3 arms

OTHER PUBLICATIONS

Stinson et al., Genes Expressed in the Male Gametophyte of Flowering Plants and their Isolation, Plant Physiol, 83:442–447 (1987).

Frova et al., Isozyme and Hsp Gene Expression During Male Gametophyte Development in maize, Current Topics in Biol. and Med. Research vol. 15, pp. 97–120 (1987).

Mascarenhas, The Biochemistry of Angiosperm Pollen Development, Bot. Rev. 41:259–314 (1975).

Frankis et al., Messenger RNA in the Ungerminated Pollen Grain: A Direct Demonstration of its Presence, Ann. Bot. 45:595–599 (1980).

Mascarenhas et al., Messenger RNAs in Corn Pollen and Protein Synthesis During Germination and Pollen Tube Growth, Theor Appl. Genet. 68:323–326 (1984).

Sari-Gorla et al., The Extent of Gametophytic-Sporophytic Gene Expression in Maize, Theor. Appl./Genet. 72:42–47 (1986).

Hanson, D. D. et al., Characterization of a Pollen Specified CDNA Clone from *Zea Mays*, and its Expression, The Plant Cell 1:173–179 (1989).

Willing, R. P. et al., An Analysis of the Quantity and Diversity of Messenger RNAs from Pollen and Shoots of *Zea Mays*, Theor Appl. Genet. 75:751–753 (1988).

ASSEMBLE FIG. 2 AS SHOWN
*fig. 2a*        *fig. 2b*
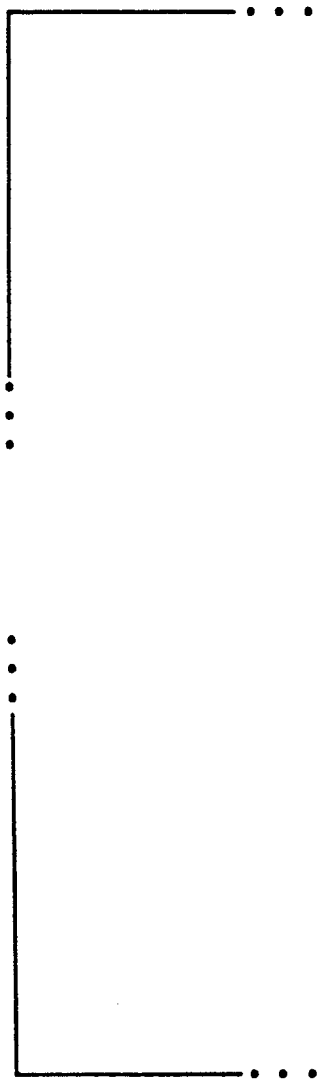 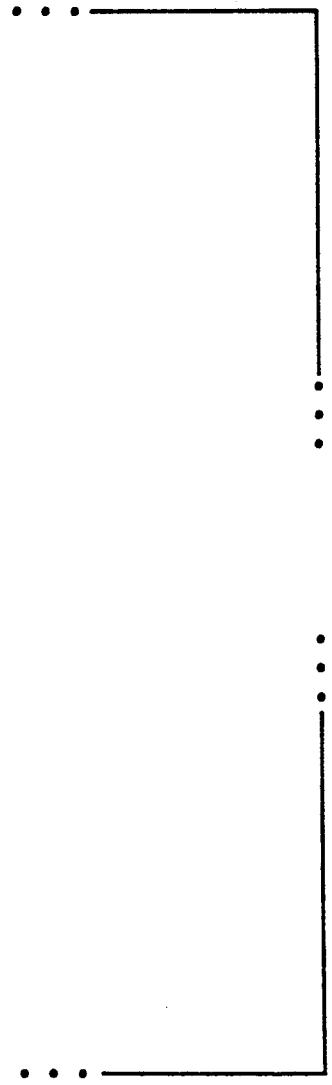
*fig. 2c*        *fig. 2d* fig. 2a

```
-1315  TACGCCAAGT  GCGTTGAAAA  TTCAAAGACC  CCGCTTGTCA
-1235  GACCTTCGGC  GTAAAGCCTT  CGTCCAGATC  GCAATCTAAA
-1155  TTGGGGACCT  TCGGCATCCG  AAGGTCCTCA  AAAACAGGAT
-1075  TCGGACTCAA  GTCAGGCATC  ACAGTAGACC  AGAATAATAC
 -995  CGGCAAGACA  GCAGCAGTTG  AAACCGACTT  AAAGATGAAA
 -915  TAAGTGTAAA  GGGCATTAAT  GTAATTTTGC  ACGGGCTACG
 -835  TCACGCTGAC  TTGGCATTCG  CTTTTGCGT   CACGCTTGTA
 -755  CGATATTTCT  GTTTGTACCT  AATAATAATA  TATAATTGTT
 -675  TTGTTTAATG  AATTTATGAA  GGTACGTCCT  TCATAACCTT
 -595  AAGGACGAAG  GACCTTAACG  ATTAATATTT  TCTATGTTGC
 -515  AGTTTGGTTA  TTCCTATTCC  ACGTGGATTA  GATGAGATTT
 -435  ACCAACTCAG  TCCCGTTCAA  TCCACATGGA  TTGAGATTAA
 -355  ATGTGTTTTT  ATAATACATC  TTGCGTGACA  TTTGTCCAAG
 -275  TATACTATTC  ACTTATGGAT  ACATTAACT   GATACCGTTT
 -195  AGATTAGAAG  TCGCAAATCC  AACTTTTGTG  GACCGCTGAA
 -115  CACAAAACTA  GGTCAAAACG  GCTTCTGCC   GTCGGCCACT
``` fig. 2b

```
GTGAATGTTG CTATTCTAGC AAAGGGAAGG TATTTTTTCG

TTTATTATTT TGAACAAATT AATATTGCGA GGGGCTACTG

TTAATAGTGT TTCTGGAGTA TAATGTGTGA ACAGATATCT

GAAGGTTGGT GAAGCGCCGA AGGTGTAAGC AGGAAAGCTT

AGGCTATTTA GACCTCAACA GATTACTATA GGTTTATTAT

TCCCGTGCCT ATAAATAGGT GAACAGTATT CCCGTACTGT

CTGTCATCTC ATTCCTATTG AAGGTACACT TGTAATTCAA

CATGTTGTCT TTTATATTCT TTATATTTCA TCCTTCGTCA

CGTCCGTAAA CCATTATATC CTAAGGGAAA TAATGCTTCG

CTTGTTCTTA ACTCATAGCA CTTGAGAACA AGTCTCCAAC

AGATAAAATT AGAAATAATT TTGACTTACT AGGGATTTAA

AACAACTATT GAGATTTTAT TGTATCAACA CTCAACACCG

TACTATGCTA AATATGAGAA GCTGCCATTT AGTGATTCTA

TGTTGAGCGC GTCTTATTTA GTTTACATA GCAGCATAGA

AAACTCAACC AAATTCGACA TATTTTTCAC CTCCCCATGC

ATTTCTACGG GCAGCCAGAC AAATCTTCGG GTCTCGCAGA
```

```
 -35 TTATTTAAGG ACACCACAGG CTGCGTTACG AAACCAGGCC
           TATA Box                         ^+1
  46 ATAATAAGGA AAGGTCCCGC CCTTTTCCTC CGACATCCAC

126 TAATGGCCTC GGTTCCGGCT CCGGCGACGA CGACCGCCGC
         ***Protein->
 206 GCTGACGACC CGAACCTCCC CGACTACGTC ATCCAGGGCC

286 CGTCACCGAG TACATCGCGG GCGCCAAGGT GAGGCTGGAG

366 ACGGGGTCAC CGACGCGACC GGCACCTACA CGATCGAGCT

446 GTGGCCAGCC CGCGCAAGGA CTGCGACGAG GTCCAGGCGC

526 CATCTCCGAC AGCCTGCGCC CGCCAACCC GCTAGGCTAC

606 AGCAGCTGGA CTCGGACGAC GACGACGACC AGTAAACTAT
                                       ***Ter
 686 GATACAGAGC GAACGCATGG CATGGATAGC AGTATCTACG

766 GTGCTTGATT CACTTGCTGC TGTCACCCAT TCCCCGTTCT

846 ATCTACGCAT GGCCTACGGT CCGCTAAAAT ATAGCCCTAA

926 GCATACGATA CAACCCACAA TTACTTATGT GTGATGGGCC
         ^Poly(A) Addition site
1006 TCATATATAT AAAACATTAA AACATATTGT CGGGGACCAT

1086 ACCCTCATCA GCGTAAAGCT GCAAAGGCCT GATGGGTGCG

1166 CCTCGCCCGA GCCTAGCCTC GGACAAGGGC AGCCGACCCC

1246 AACATATTTC CGGCTCGCCC GAGGCCCTGT CTTCGCCAAG

1326 GCAGGAGCAT TTAATGCAAA GGTGGCCTGA CACATTTATC
```

*fig. 2c*

```
       AGATTTGCCA CCCTCGTCTC ACCCTCCCTC CCTCACACAA
mRNA
       AAGGGGGGAG GGGAAAACAC GTACATTCAC CCGGCGGCAA

CGTCATCCTA TGCCTATGCG TCGTCCTCTC CTGTGCCGCG

GCGTGTACTG CGACACCTGC CGCGCCGGGT TCGTGACCAA

TGCAAGCACT TCGGCACCGG CAAGCTCGAG CGCGCCATCG

CAAGGACAGC CACGAGGAGG ACATCTGCCA GGTGGTGCTG

TCAGGGACCG CGCCGGCGTC CTGCTCACCA GGAACGTTGG

TTCAAGGACG TGCCGCTCCC CGTCTGCGCC GCGCTGCTCA

ACCACGGCGG CGTCGCGGAC ATGCTGCACA AAACTACAAC

GAAAGAAAAG GAAGAAAAGG AAAATAAAAA ATGTATCAGA
                                ******Poly(A)signal
       TAACATAACA TGTGGGCCGG CTTGGCCCAG GCACAAGCCC

TTATGAGCCG TGTTGTGCCG TCACATGGAT CGATCCAGCG

GGCCAAAAAA GCCTAAGATG TCGTAGTGTG CTAGACCGAC

AATTAGGGGT ACCCTTAAGG CTCCTAATTC TCAGCTGGTA

ATTAAGTCAG GGATCAGTCC ATTCGAGGGA CTCGATCACG

GGAGGATCTC CGTCTCGCCC GAGGCCCTCC TCCAGCGGCG

AAGCAACCCT GACCAAATCG CCGCACCGAC CGACCAAATC

CTGAGCGCCC TTCAGCCGAC AGAGCCGAAG
```

*fig. 2d*

ISOLATED POLLEN-SPECIFIC PROMOTER OF CORN

STATEMENT OF RIGHTS UNDER FEDERALLY-SPONSORED RESEARCH

This invention was made with government support under grant DCB 85-01461 awarded by The National Science Foundation. The government has certain rights in the invention.

RELATED APPLICATION

This application is a continuation-in-part of application Ser. No. 07/341,151 filed Apr. 20, 1989 now abandoned.

TECHNICAL FIELD

This invention relates generally to the field of recombinant genetics, and specifically to the use of a pollen-specific promoter for regulating expression of genes in plants.

BACKGROUND OF THE INVENTION

Traditional methods of cross-breeding plants have been used to introduce desirable genetic traits from one plant to another, and the production of so-called hybrid seeds is crucial to the agricultural industry. However, in order to obtain hybrid seeds, the self-pollination of a plant must be prevented.

Pollen production can be prevented by applying to the plant or soil a chemical composition such as those disclosed in U.S. Pat. No. 4,801,326 issued to Ackmann et al. A preferred use of such compounds is to apply them 2-4 times at intervals of 3 to 10 days in order to maximize inhibition of pollen production in the female plants. Hybrid seeds are then produced by the cross fertilization of the female plants by pollen from adjoining rows of non-treated plants. Although this method may prevent pollen production, it is labor-intensive and may require close attention to the developmental stage of the plants for timely application of the chemical composition. In addition, this method presents potential problems with toxicity of chemicals introduced into the environment.

Some plants, such as corn and sugar beet, contain a cytoplasmic gene(s) for male sterility which results in the absence of pollen production. U.S. Pat. No. 3,861,079 (Patterson) discloses procedures for using inbred lines of maize carrying male sterile genes. However, the presence of certain cytoplasmic male sterility genes is accompanied by a sensitivity to certain fungal pathogens, and for many plants cytoplasmic male sterility genes are not available.

A method of inhibiting pollen production without relying on endogenous plant genes or application of chemicals to crops or to soil would be very beneficial to the agricultural industry. By using genetic manipulation techniques to insert a gene which will inhibit only pollen production into the genome of a plant, reliance on naturally occurring male sterility genes will be unnecessary.

The use of a plant promoter and an exogenous gene to effect changes in the genetic make-up of plants is known, in the art. European Patent Application No. 0122791 (Hall et al.) discloses the use of a DNA shuttle vector comprising T-DNA and a plant structural gene. The specific application disclosed by Hall et al. is to enhance protein content and nutritional value of crops such as alfalfa by causing expression of the gene for the seed storage protein phaseolin. T-DNA is used because it can be stably integrated into transformed plant cell genomes. European Pat. Application No. 0126546 (Kemp et al.) discloses the enhancement of the protein content of crops by using a plant structural gene in combination with a T-DNA promoter instead of the plant promoter for that particular structural gene. U.K. Patent Application No. 2,187,462 (Marcker et al.) discloses the use of a root nodule promoter with root nodule-specific genes or other genes to establish nitrogen-fixing capacity in non-leguminous plants and to add new traits, such as resistance to herbicides, diseases and pests. Such promoters are only functional in root nodules. The Hall and Kemp patents teach the use of T-DNA as the vector for incorporating a promoter and structural gene into the plant genome. In each case the utility requires the expression of the structural gene associated with either the plant promoter or the T-DNA promoter. These patents do not teach the use of pollen-specific promoters to initiate transcription and translation of either endogenous or exogenous genes.

A need thus exists for a method of inducing male sterility in plants without relying on traditional breeding methods or on applications of chemicals to plants or soil.

SUMMARY OF THE INVENTION

The present invention satisfies this need by providing a pollen-specific promoter which can be combined with genes, the expression of which in pollen is desired. Isolation of a pollen-specific promoter region, its nucleotide sequence, and its use in regulating the production of pollen and the characteristics of pollen is provided.

As a result of developments in our laboratory in the area of genetic engineering with our pollen-specific promoter, it is now possible to introduce into the genome of a plant a foreign gene which will regulate or inhibit pollen production. The foreign gene is inserted after, i.e. 3' to the pollen-specific promoter and in place of the pollen-specific genes. The usefulness of this technique is not limited to inducing male sterility in plants. The foreign gene may also code for toxicity to insects and other pests for which pollen might be used as food by the pest, and for other traits such as enhanced nutritional value of the pollen.

BRIEF DESCRIPTION OF THE DRAWINGS

These and other objects, features and advantages of the present invention will be more fully understood from the following detailed description when read in conjunction with the accompanying drawings, in which:

FIG. 2a-d represent the nucleotide sequence of the promoter region of Zm13, its coding region and 3' flanking region.

Figure 1:
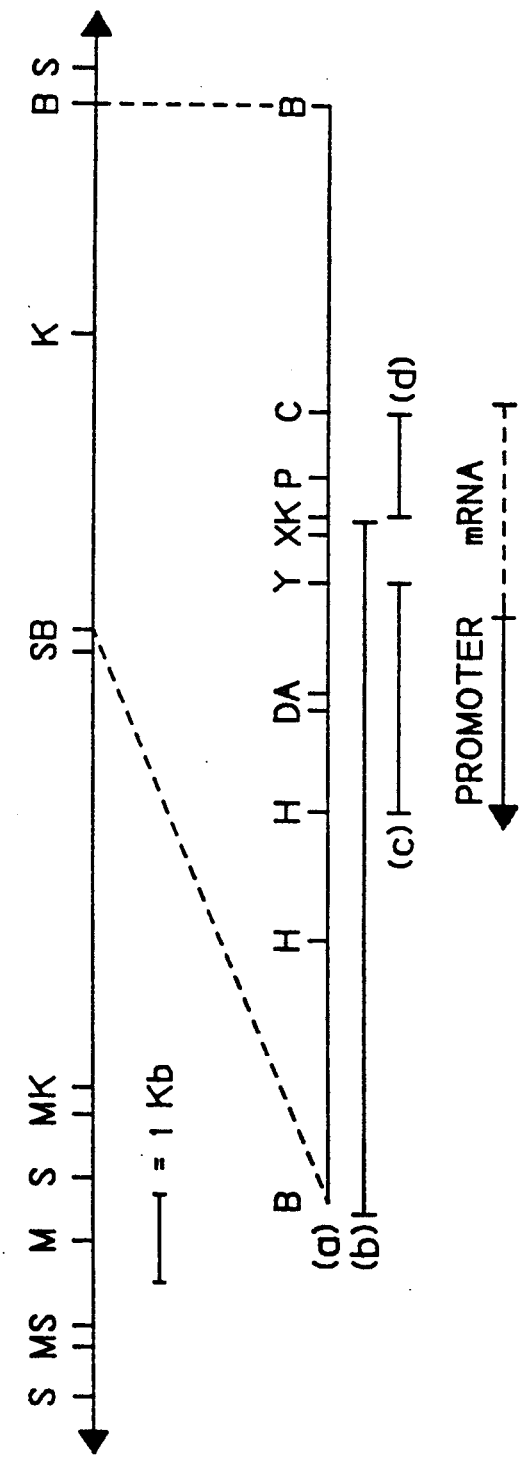
FIG. 1 represents the restriction map of genomic clone Zm13, in which the positions of several restriction enzyme sites are indicated and the position of the promoter region is identified.

DETAILED DESCRIPTION OF THE INVENTION a. Summary of Preliminary Research

In flowering plants, the early development of the male gametophyte (pollen) occurs in a young flower bud within the anther after meiosis is complete. The microspores, on release from the tetrad, increase rapidly in size and undergo a change in shape. In corn, microspore mitosis occurs after a long interphase of 7-9 days. (C. Frova, G. Binelli, E. Ottaviano (1987) Isozyme and hsp Gene Expression During Male Gametophyte Development in Maize. In M. C. Rattazzi, J. G. Scandalios, G. S. Whitt, eds, Isozymes: Current Topics in Biological and Medical Research, Vol. 15: Genetics, Development, and Evolution. Alan R. Liss, New York, pp 97-120). Microspore mitosis results in a vegetative cell which contains the bulk of the cytoplasm of the microspore and a generative cell which inherits a very small amount of cytoplasm and is surrounded by the cytoplasm of the vegetative cell.

In the pollen of several plant species including corn the generative cell divides in the pollen grain producing two sperm cells. Following anther dehiscence the pollen grain is deposited on the stigma of the pistil in a flower where it begins another phase of its development by germinating and producing a pollen tube which grows down into the style. This phase of development is unlike the type of development prior to anthesis and consists largely of tube cell wall synthesis and the synthesis of cell membrane to accompany the rapid increase in length of the tube. (J. P. Mascarenhas (1975) The Biochemistry of Angiosperm Pollen Development. Bot. Rev. 41:259-314). To reach the embryo sac, pollen tubes grow to appreciable lengths within relatively short periods of time; in corn the silks can reach lengths of 40-50 cm. Thus, although the development of the male gametophyte is relatively simple in comparison to the sporophyte, there are a number of discrete events and types of differentiation that occur during its life.

We have for a number of years been interested in the regulation of various molecular events during the development of the male gametophyte. (See J. R. Stinson, Eisenberg, A. J., Willing, R. P., Pe, M. E., Hanson, D. D. and Mascarenhas, J. P. (1987) Genes Expressed in the Male Gametophyte of Flowering Plants and Their Isolation. Plant Physiol. 83:442-447.)

The mature pollen grains of several plant species contain mRNAs that were synthesized prior to anthesis. These mRNAs have been isolated and in cell free translation systems code for polypeptides that are similar to those synthesized during pollen germination and pollen tube growth. (R. C. Frankis, J. P. Mascarenhas (1980) Messenger RNA in the Ungerminated Pollen Grain: A Direct Demonstration of its Presence. Ann. Bot. 45:595-599; N. T. Mascarenhas, D. Bashe, A. Eisenberg, R. P. Willing, C. M. Xiao, J. P. Mascarenhas (1984) Messenger RNAs in Corn Pollen and Protein Synthesis During Germination and Pollen Tube Growth. Theor. Appl. Genet. 68:323-326). In many pollens these presynthesized mRNAs appear to be required during pollen germination and early tube growth. (J. P. Mascarenhas, 1975).

An analysis of the kinetics of hybridization of cDNA with poly(A)RNA in excess has been carried out with poly(A)RNA isolated from mature pollen of *Tradescantia paludosa* (R. P. Willing, J. P. Mascarenhas (1984) Analysis of the Complexity and Diversity of mRNAs from Pollen and Shoots of Tradescantia. Plant Physiol 75:865-868) and maize, (R. P. Willing, D. Bashe, J. P. Mascarenhas (1988) An Analysis of the Quantity and Diversity of Messenger RNAs from Pollen and Shoots of *Zea mays*. Theor Appl. Genet. 75:751-753.) The mRNAs in mature pollen consist of three abundant classes. The first class, which is a relatively small fraction of the total poly(A)RNA of the pollen grains, is low in complexity, and consists of a few different mRNAs which are extremely prevalent, each being present in 26,000 and 32,000 copies per pollen grain of *T. paludosa* and maize, respectively. The mRNAs of the second class which make up the bulk of the mRNAs, are intermediate in number and in reiteration frequency. The most complex class of mRNAs is made up of 17,000 to 18,000 different sequences each present on an average in 100-200 copies per pollen grain. The total complexity of the pollen mRNAs in both *T. paludosa* and maize is very similar, being in excess of $2 \times 10^7$ nucleotides. The mRNAs in the mature pollen grains of both plants are the products of approximately 20,000 different genes. There are thus a large number of genes involved in pollen development.

cDNA libraries to poly(A)RNA from mature pollen of maize have been constructed. Based on colony hybridizations of a large number of clones from the libraries, using $^{32}$P-cDNAs from pollen and vegetative tissues as probes, it is estimated that about 10% of the total genes expressed in maize pollen might be specific to pollen (Stinson et al., 1987). In maize about 72% of the isozymes studied were expressed in both pollen and sporophyte, whereas only 6% of the isozymes were pollen-specific. (M. Sari-Gorla, C. Frova, G. Binelli, E. Ottaviano (1986) The Extent of Gametophytic-Sporophytic Gene Expression in Maize. Theor. Appl. Genet. 72:42-47). Thus, only a relatively small percentage of the total number of genes expressed during pollen development are specific to pollen, that is, expressed only in pollen and not in other tissues of the plants.

b. Use of Cloned Libraries to Study Gene Expression in Pollen.

The libraries constructed contain clones that represent mRNAs that are present in mature pollen. Several of these clones, both pollen-specific and those shared with the sporophyte, have been used as probes to study the stage of pollen development when the genes first are activated and to study the pattern of accumulation of the mRNAs. Such Northern analyses have shown that all the clones that have been studied thus far represent genes that are first activated after microspore mitosis. The mRNAs accumulate thereafter reaching a maximum concentration in the mature pollen grain just prior to anthesis. (Stinson, et al. 1987)

c. Characterization of a Pollen-Specific Gene From Maize

One of the cDNA clones from the library, Zm13, was selected for detailed characterization. This clone is pollen-specific. Northern analysis shows that Zm13 hybridizes to a mRNA of approximately 985 nucleotides in length that is found only in pollen but not in RNA isolated from shoots, roots, kernels, ovules or silks. D. D. Hanson, D. A. Hamilton, J. L. Travis, D. M. Bashe, J. P. Mascarenhas (1989) Characterization of a Pollen Specific cDNA Clone from *Zea mays* and its expression. The Plant Cell 1:173-179. Zm13 represents a gene that is present in a very few copies in the corn genome. The cDNA has been sequenced. It is 929 nucleotides in length and in addition has a 47 nucleotide poly(A) tail. Primer extension analysis indicates that Zm13 is a full length copy of the mRNA, which codes for a predicted polypeptide that is 170 amino acid residues long and has a molecular weight of 18.3 kD. The hydropathy profile strongly suggests a signal peptide at the amino terminus. The function of this protein is not yet known. A computer search of the nucleotide and protein sequence data bases has not revealed any meaningful homology with known proteins (Hanson et al., 1989).

A genomic clone corresponding to Zm13 was isolated by screening a genomic library of the inbred maize line W-22. The cDNA clone is colinear with the genomic clone with no introns being present. The genomic clone consists of a region more than 15 kilobase pairs in length. A region of greater than 1300 bp 5' to the start of transcription and over 500 bp 3' to the termination of transcription has been sequenced. This sequence is shown in FIG. 2.

In situ hybridizations using single stranded $^{35}$S-labeled riboprobes demonstrate that the mRNA is present in the cytoplasm of the vegetative cell in the mature pollen grain. The silver grains are uniformly distributed throughout the vegetative cell cytoplasm. The Zm13 mRNA is also uniformly present throughout the pollen tube cytoplasm after germination. Zm13 mRNA is thus a product of the vegetative cell nucleus rather than the generative cell or sperm cells.

Sequencing data of both the cDNA and genomic DNA have shown the position of the coding region of Zm13 mRNA to be as indicated by the dotted line in FIG. 1. Various subclones have been constructed, and a few of these are shown in FIG. 1. Several of the subclones include various lengths of 5' upstream sequences and also 3' downstream sequences that can be used in contructs that contain the promoter region, a foreign gene and 3' flanking regions.

Gene expression, including organ- and tissue-specific control, has often been found to be exerted mainly through regions of upstream DNA sequences. Deletion of material upstream or downstream from the suspected control region can be used to identify the boundaries of the promoter. Promoter regions including enhancers are characterized by their ability to bind to RNA polymerase and other activating proteins, and generally contain certain recognition sites for the various proteins.

Generally, point mutations which affect promoter and enhancer functions of the DNA might be expected to occur in these recognition sites. Mutations, base substitutions and other changes can occur outside the recognition sites without affecting promoter or enhancer function. However, the distance or number of nucleotides between the recognition sites appears to have a role in allowing the DNA to assume a configuration necessary to permit interaction of the DNA with RNA polymerase and other proteins involved in transcription.

The nucleotide sequence of the upstream region of clone Zm13 has characteristics of a promoter. Tissue specific promoter sequence elements are known to reside within several hundred base pairs of the start of transcription. (See review by C. Kuhlemeier, P. J. Green, N.-H. Chua (1987). Regulation of Gene Expression in Higher Plants. Ann. Rev. Plant Physiol. 38:221-257.) In addition, enhancer elements have been located in introns and in the 3'-flanking regions of genes. Based on current knowledge about tissue-specific promoters in plants, the clone Zm13 contains the promoter region. Using the Zm13 promoter it is now possible, using standard techniques, to introduce into plants a nucleotide construct, or vector, containing the promoter and one or more genes endogenous or exogenous to the plant. In this way the expression of genes in pollen can be regulated.

Techniques for introducing a vector into plant cells are known in the art. See, for example, Perani et al. (1986) Physiol. Plantarum 68:566. Naturally occurring plant DNA and RNA viruses can be used, and inoculation can be accomplished by rubbing the leaves with the engineered virus. However, at this time use of viral vectors is limited by their ability to infect only their natural hosts.

The most developed vector for inserting genes into plants is Agrobacterium tumefaciens, which infects many plants that become susceptible to infection following wounding. Other methods of introducing DNA into plants include electroporation, chemically-mediated DNA uptake, and the use of microprojectiles. Microprojectiles have been used to stably integrate an intact engineered gene into corn cells. (T. M. Klein, M. Fromm, A. Weissinger, D. Tomes, S. Schaaf, M. Sletter, J. C. Sanford. (1988) Transfer of Foreign Genes into Intact Maize Cells with High-Velocity Microprojectiles. PNAS 85:4305. See also, D. E. McCabe, W. F. Swain, B. J. Martinelli and P. Christon. (1988) Stable Transformation of Soybean (Glycine Max) by Particle Acceleration. Bio/Technology 6:923-926.) Workers skilled in the art will be familar with these methods.

Techniques known in the art for introducing the pollen-specific promoter and exogenous or endogenous gene(s) can be used to introduce genes into plants for the purpose of preventing pollen development, specifically, suicide genes which would result in abortion of pollen development and hence male sterility. Such genes include those that produce a toxic compound or a hydrolytic enzyme such as DNase. The methods discussed here can also be used to provide pollen with new characteristics. Genes of interest for use with corn and other plants include proteins which are toxic to insects and other pests that consume pollen, and proteins which enhance the nutritive value of pollen.

The following examples are offered by way of illustration and not by way of limitation.

EXAMPLE 1

Construction of a cDNA Library from Pollen and Clone Selection by Library Screening A cDNA library made to poly(A)RNA isolated from mature pollen of maize was constructed in a modified Okayama-Berg type plasmid such as that described in Alexander, D. C., et al., (1984), Gene 31:79-89. The dimer-primer was identical to the pARC7 plasmid described in the publication, with the exception that it did not contain the polylinker fragment. The cloning procedures used to make the maize cDNA library were essentially those described by Alexander et al. The construction of the library has been described (Stinson et al., (1987) Plant Physiol. 83:442-447). The resultant library consists of several thousand clones. Comparison of colony hybridizations to $^{32}$P-labeled cDNA from pollen versus $^{32}$P-labeled cDNA from vegetative tissues provided for the selection of pollen-specific and shared clones. Likely candidates were further screened by Northern analysis as follows: total RNA was prepared from maize pollen, shoots, roots, kernels, ovules, and silks, and electrophoretically separated in a 1.5% agarose gel containing 2.2M formaldehyde and transferred to nitrocellulose membranes according to the manufacturer's instructions (New England Nuclear, Instruction Manual, 1982). Individual filters were prehybridized and probed with $^{32}$P-labeled cDNAs from candidate clones. Pollen-specific cDNAs were identified by their hybridization to only RNA from mature pollen. Likewise, clones representing shared messages displayed hydridization to RNA from additional tissues, as well as to RNA from pollen.

Screening of the genomic library was then performed to retrieve pieces of genomic DNA which hybridized with the pollen-specific or shared cDNAs used as probes. The screening procedure was virtually as described in Maniatis, T., et al., (1982) Molecular Cloning: A Laboratory Manual, Cold Spring Harbor Laboratory, Cold Spring, N.Y. Briefly, cDNA plasmids were isolated and made radioactive by the incorporation of [alpha-$^{32}$P]dCTP via nick-translation as described in Maniatis et al. (1982). These were then used to probe nylon membranes representing duplicate plaque lifts of the genomic library. After autoradiography to determine areas of hybridization, the corresponding plaques were collected off the original plates, amplified, retitered, and replated for repeat hybridizations. This was continued until hybridizing plaques were purified away from non-hybridizing plaques.

EXAMPLE 2

Construction of a Genomic Library

A library containing DNA representing the entire maize genome was made from etiolated maize seedlings utilizing the vector EMBL 3 (available commercially from Promega Biotech). The genomic DNA was collected from maize seedling tissue by the procedure of Riven et al. with slight modifications. (Riven, C. J., et al. (1982) In: Maize for Biological Research. ed. W. F. Sherridan. Plant Molecular Biology Association and University of North Dakota Press.) The library was constructed by partial Sau 3A digestion of the genomic DNA. The DNA was size fractionated, and pieces of 10–20 kilobasepairs (Kb) were collected for ligation into EMBL 3 arms prepared by the method of Frischauf, A., et al. (1983) J. Mol. Biol. 170:827–842, as given in the Promega Biotech catalogue 1985/86, page DB25. The ligation mix was then packaged (Gigapack, Stratagene) and titered, resulting in a genomic library (Maniatis, T., et al. 1982).

EXAMPLE 3

The Isolation and Subcloning of Zm13

See D. D. Hanson, D. A. Hamilton, J. L. Travis, D. M. Bashe and J. P. Mascarenhas, (1989), Characterization of a Pollen-Specific DNA Clone from *Zea mays* and its Expression. The Plant Cell 1:173–179. One of the clones which was shown to be pollen-specific by Northern analysis, labeled Zm13, produced a positive plaque upon screening the genomic library. This plaque was isolated, purified, and amplified. The DNA from a 300 ml culture of Zm13-infected Q359 cells was isolated by extraction and ultracentrifugation as described in Focus 8:2 (Bethesda Research Laboratories). The isolated phage DNA contained an insert of approximately 15 Kb of genomic DNA. Restriction mapping of the genomic clone produced the map represented by the top line in FIG. 1. Restriction digestion of the genomic clone followed by agarose gel electrophoresis and Southern analysis (Southern, E. M. (1975) Detection of Specific Sequences among DNA Fragments Separated by Gel Electrophoresis. J. Mol. Biol. 98:503–517) revealed the hybridization of the cDNA clone Zm13 to a 5.4 Kb BamHI fragment. The isolated and purified BamHI fragment was subcloned into the plasmid vector pUC13 (Bethesda Research Laboratories) in a ligation reaction containing approximately 500 ng of isolated insert, 200 ng of phosphatased BamHI-cut pUC13, 2 units of T4-DNA Ligase (Boehringer Mannheim Biochemicals), in a solution comprising 20 mM Tris:HCl pH 7.6, 10 mM MgCl$_2$, 10 mM dithiothreitol, 10 mM ATP. All subsequent ligation reactions were performed virtually identically to this. Restriction analysis of the subcloned fragment produced the map shown by the second line of FIG. 1. Portions of this 5.4 Kb insert were further subcloned in the plasmid vector pBS+ (Stratagene) via digestion with the appropriate restriction enzyme and ligation as described above, resulting in several subclones, some of which are shown in FIG. 1.

Sequencing data of both the cDNA and genomic DNA have shown the position of the transcribed messenger RNA of the Zm13 gene to be as shown by the dotted line in FIG. 1. The clones which extend beyond the transcription start site, therefore, contain "upstream" regions. Gene expression, including organ- and tissue-specific control, has often been found to be exerted through regions of upstream DNA sequences, so any upstream pollen-specific control regions are likely to be represented in one or more of these clones (Kuhlemeier et al., 1987). However, control regions have also occasionally been shown to exist within and 3' ("downstream") to the transcribed region. We have cloned and sequenced a region of more than 500 base pairs located 3' to the transcribed region. Therefore, other areas of Zm13 which are present in one or more of our clones may also contain pollen-specific elements.

Since modifications will be apparent to those skilled in the art, it is intended that the invention be limited only by the scope of the appended claims.

What is claimed is:

1. A purified isolated DNA sequence consisting essentially of the promoter region derived from a pollen-specific gene of inbred corn line W-22 having substantially the sequence illustrated in FIG. 2 and any base substitutions, additions, deletions, mutations and other changes thereof in which the promoter function is preserved.

* * * * *